United States Patent [19]
Knutsen et al.

[11] Patent Number: 5,430,027
[45] Date of Patent: Jul. 4, 1995

[54] 2-CHLORO-N⁶-SUBSTITUTED ADENOSINES, THEIR PHARMACEUTICAL COMPOSITIONS, AND ACTIVITY IN TREATING ISCHEMIAS

[75] Inventors: Lars J. S. Knutsen, Vedbӕk; Jesper Lau, Farum, both of Denmark

[73] Assignee: Novo Nordisk A/S, Bagsvaerd, Denmark

[21] Appl. No.: 61,892

[22] Filed: May 14, 1993

[30] Foreign Application Priority Data

May 14, 1992 [DK] Denmark .................. 0625/92

[51] Int. Cl.⁶ .................... A61K 31/70; C07H 19/167
[52] U.S. Cl. .................... 514/46; 536/27.62; 536/27.63; 536/27.70
[58] Field of Search ............ 514/46; 536/27.62, 27.63

[56] References Cited

U.S. PATENT DOCUMENTS

| | | | |
|---|---|---|---|
| 3,590,029 | 6/1971 | Koch et al. | 536/27.62 |
| 3,796,700 | 3/1974 | Yoshioka et al. | 536/27.62 |
| 3,819,613 | 6/1974 | Marumoto et al. | 536/27.62 |
| 4,704,381 | 11/1987 | Shaumann et al. | 514/46 |
| 5,155,098 | 10/1992 | Effland et al. | 514/46 |

FOREIGN PATENT DOCUMENTS

| | | | |
|---|---|---|---|
| 0253962 | 1/1988 | European Pat. Off. | 514/46 |
| 0490818 | 6/1992 | European Pat. Off. | 514/46 |
| 2131938 | 1/1972 | Germany | 536/27.62 |
| 2163790 | 7/1972 | Germany | 536/27.62 |
| 40-10979 | 6/1965 | Japan | 536/27.62 |
| 1123245 | 8/1968 | United Kingdom | 536/27.62 |
| WO85/04882 | 11/1985 | WIPO | 536/27.62 |
| WO91/04032 | 4/1991 | WIPO | 514/43 |

OTHER PUBLICATIONS

Fujii et al. (III), "Purines. XII. Catalytic Hydrogenation of Alkoxyaminopurines and Related Derivatives," *Chem. Pharm. Bull.*, 21(8), 1835–1838 (1973).

Fujii et al. (IV), "Purines. XI. The Synthesis of N-Alkoxyadenosines and Their 2′,3′-Isopropylidene Derivatives," *Chem. Pharm. Bull.*, 21(8), 1676–1682 (1973).

Fleysher (I), "N⁶-Substituted Adenosines: Synthesis, Biological Activity, and Some Structure–Activity Relationships," *J. Med. Chem.*, 15(2), 187–191 (1972).

Fleysher (II), "Synthesis and Biological Activity of Some New N⁶-Substituted Purine Derivatives," *J. Med. Chem.*, 12(11), 1056–1061 (1969).

(List continued on next page.)

*Primary Examiner*—Douglas W. Robinson
*Assistant Examiner*—L. Eric Crane
*Attorney, Agent, or Firm*—Steve T. Zelson; Elias J. Lambiris

[57] ABSTRACT

Adenosine compounds having the following structure

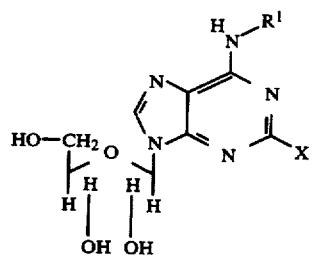

wherein X is halogen, perhalomethyl, acetamido, cyano, $C_{1-6}$-alkoxy, $C_{1-6}$-alkylthio or $C_{1-6}$-alkylamino; and $R^1$ is —$NR^2R^3$ or $YR^4$, wherein Y is oxygen or sulfur;

$R^2$ is phenyl, $C_{1-6}$-alkyl or substituted $C_{1-6}$-alkyl; and $R^4$ is naphthyl, partly saturated naphthyl; optionally phenyl or phenoxy substituted $C_{1-6}$-alkyl wherein the phenyl and phenoxy substituents are also optionally substituted, or optionally phenyl or phenoxy substituted $C_{3-8}$-cycloalkyl and their pharmaceutically acceptable salts are useful in the treatment of myocardial and cerebral ischemias.

19 Claims, No Drawings

OTHER PUBLICATIONS

Kampe et al., "Adenosines," S. African Patent 67 07,630; Apr. 25, 1968; *Chem. Abstr.*, 70, p. 394, Abstr. No. 88212z (1969); only Abstract supplied.

Giner-Sorolla et al., "The Synthesis and Biological Properties of Hydroxylaminopurines and Related Derivatives," *J. Med. Chem.*, 11(3), 521–523 (1968).

Hori et al., "Beneficial Role of Adenosine in Myocardial Ischemic and Reperfusion Injury," *Drug. Develop. Res.*, 28, 432–437 (1993).

Shugar et al., "New Light on Tautomerism of Purines and Pyrimidines and Its Biological and Genetic Implications," *J. Biosci.*, 8(3–4), 657–668 (1985); *Chem. Abstr.*, 104(25), p. 208, Abstr. No. 220507b (1986); only Abstract provided.

Fleysher et al., "9-β-D-Ribofuranosylpurin-6-yl-p-[bis(2-chloroethyl)amino]benzylidenehydrazone. The Synthesis of an Adenosine Derivative Containing a Nitrogen Mustard," in *Nucleic Acid Chem.*, vol. 2, 1978, Townsend et al. eds., John Wiley & Sons, New York, pp. 667–671.

McCartney et al., "Carcinogenic N-Hydroxylaminepurine Derivatives Do Not Act as Base Analog Mutagens in *Salmonella Typhimurium*," *Mutation Research*, 144, 231–237 (1985).

Huang et al., "Effect of Adenosine on Cyclic AMP Accumulation in Ventricular Myocardium," *Biochemical Pharmacology*, 25, 2713–2719 (1976).

Kusachi et al., "Dog Coronary Artery Adenosine Receptor: Structure of the $N^6$-Alkyl Subregion," *J. Med. Chem.*, 28, 1636–1643 (1985).

Fujii et al., "Purine. XXIX. Syntheses of 9-Alkyl-2-deuterio-$N^6$-Methoxyadenines and 2-Deuterio-$N^6$,9-dimethyladenine: Tautomerism in 9-Substituted $N^6$-Alkoxyadenines," *Chem. Pharm. Bull.*, 35(11), 4482–4493 (1987).

2-CHLORO-N⁶-SUBSTITUTED ADENOSINES, THEIR PHARMACEUTICAL COMPOSITIONS, AND ACTIVITY IN TREATING ISCHEMIAS

The present invention relates to modified adenosine derivatives having a substituent at the 6-position containing sulphur, oxygen or nitrogen, further substituted at the purine 2-position as well as pharmaceutically acceptable addition salts thereof having central nervous system (CNS) properties. Also covered are processes for preparation of the above derivatives and their pharmaceutical compositions as well as methods for using the compounds and compositions as drugs primarily for CNS ailments.

BACKGROUND OF THE INVENTION

Adenosine can be considered to be a hormone which has been shown to have a number of significant effects on the mammalian central nervous system [Annual Reports in Medicinal Chemistry, 1988, 23, 39–48; International Review of Neurobiology (Smythies, J. R. and Bradley, R. J., eds.) Academic Press Inc., 1985.27, 63–139], especially under conditions of neuronal stress where the compound appears to act as an endogenous neuroprotectant (Progress in Neurobiology, 1988, 31,85–108, Trends in Pharmacological Sciences, 1983, 9, 193–194). For example, the concentration of adenosine has been demonstrated to rise greatly in certain brain regions following epileptic seizures or conditions of neuronal ischaemia/anoxia (Brain Research 1990, 516, 248–256).

It has been established for some years now that centrally acting adenosine receptor agonists or compounds which increase extracellular adenosine levels can exhibit what is termed neuromodulator activity. Such substances influence the release of neurotransmitters in regions of the central nervous system (Annual Review of Neuroscience, 1985, 8, 103–124; Trends in Neurosciences, 1984, 164–168), with particular inhibitory effects on the release of the excitatory amino acid glutamic acid (glutamate) (Nature, 1985, 316, 148–150, Journal of Neurochemistry, 1992, 58, 1683–1689).

There are several CNS ailments for which this adenosine receptor mediated neuromodulator activity could be of clear therapeutic benefit. Examples of these would include the treatment of convulsive disorders (European Journal of Pharmacology, 1991, 195, 261–265; Journal of Pharmacology and Experimental Therapeutics, 1982, 220, 70–76), prevention of neurodegeneration under conditions of brain anoxia/ischaemia (Neuroscience Letters, 1987, 83, 287–293; Neuroscience, 1989, 30, 451–462; Pharmacology of Cerebral Ischaemia 1990 (Kriegelstein, J. and Oberpichler, H., Eds., Wissenschaftliche Verlagsgesellschaft mbH: Stuttgart, 1990, pp 439–448) or the use of a purinergic agent in the treatment of pain (European Journal of Pharmacology, 1989, 162, 365–369; Neuroscience Letters, 1991, 121, 267–270). In addition, the antiischaemic effect of the compounds described within this invention may be useful in protecting against cardiac ischaemia.

Adenosine receptors represent a subclass (P1) of the group of purine nucleotide and nucleoside receptors known as purinoreceptors. This subclass has been further classified into two distinct receptor types which have become known as A1 and A2. Extensive research has been carried out in a quest to identify selective ligands at these sites [see, for example, Comprehensive Medicinal Chemistry Volume 3, (Hansch, C., Sammes, P. G. and Taylor, J. B., Eds., Pergamon Press PLC: 1990, pp 601–642)]. Selective ligands exist for A1 and A2 adenosine receptors and the structure-activity relationships of the various reference ligands have been reviewed (Biochemical Pharmacology, 1986, 35, 2467–2481) together with their therapeutic potential (Journal of Medicinal Chemistry, 1992, 35, 407–422). Among the known adenosine receptor agonists most selective for the A1 receptor over the A2 receptor are the examples where the adenine nucleus is substituted with a cycloalkyl group on the amino function, for example N-cyclopentyladenosine and N-cyclohexyladenosine (Journal of Medicinal Chemistry, 1985, 28, 1383–1384) or 2-chloro-N-cyclopentyladenosine (Naunyn-Schmiedeberg's Arch pharmacal. 1988, 337, 687–689).

Examples of adenosine derivatives in the chemical literature with the heteroatoms, oxygen or nitrogen bonded directly to the 6-amino substituent are summarised below.

Examples with hydrogen at the purine 2-position include N-aminoadenosine, N-[(N-methyl-N-phenyl)amino]adenosine, N-hydroxyadenosine, N-methoxyadenosine and N-benzyloxyadenosine (Journal of Medicinal Chemistry, 1985, 28, 1636–1643); N-ethoxyadenosine (Chemical and Pharmaceutical Bulletin, 1973, 21, 1676–1682; ibid., 1973, 21, 1835–1838); N-(methylamino)adenosine and N-[(N-hydroxy-N-methyl)amino]adenosine (Journal of Medicinal Chemistry, 1968, 11, 521–523).

Examples of adenosine derivatives with oxygen or nitrogen atoms bonded to the 6-amino substituent, containing an additional purine 2-substituent are 2-amino-N-hydroxyadenosine (Journal of Medicinal Chemistry, 1972, 15, 387–390); 2-amino-N-aminoadenosine (Chemical and Pharmaceutical Bulletin, 1969, 17, 2373–2376); 2-amino-N-methoxyadenosine (Chemical and Pharmaceutical Bulletin, 1975, 23, 464–466); 2-chloro-N-hydroxyadenosine (Journal of Medicinal Chemistry, 1991, 34, 2226–2230), 2-fluoro-N-aminoadenosine (Journal of Medicinal Chemistry, 1970, 13, 427–430) and 2-fluoro-N-hydroxyadenosine (Journal of Medicinal Chemistry, 1971, 14, 816–819).

In the above scientific articles, no mention is made of any pharmacological effects of the compounds concerned on the central nervous system.

In U.S. Pat. No. 3,819,613, substituted adenosine analogues with hydrazone derivatives on the 6-amino function are disclosed as hypotensive agents. In GB 1,351,501, adenosine and 2-aminoadenosine derivatives having a —NH—R$_2$ group joined to the 6-amino function are disclosed as coronary dilators and platelet aggregation inhibitors. In EP A 152,944, a series of 2-, 6- and 8-substituted adenosine derivatives are described having activity as anti-allergy agents. In EP A 253,962, adenosine and 2-haloadenosine analogues having an alkyl, cycloalkyl or an aralkyl group attached to the 6-amino function are described with activity as anti-dementia agents. In EP 402,752A, derivatives of adenosine unsubstituted in the 2-position are described which have a substituted heteroaromatic 1-pyrrolyl moiety attached to the 6-amino group. In WO 91/04032, methods of preventing neural tissue damage in neurodegenerative diseases by increasing extracellular concentrations of adenosine are described. Examples are given of prodrug esters of AICA riboside (5-amino-1-β-D-ribofuranosyl)imidazo-4-carboxamide) which are claimed to be centrally acting neuroprotective agents. In WO 92/02214, analogs of AICA riboside are revealed for the treatment of myocardial and cerebral ischaemias. In WO 90/05526, 2-(alkylalkynyl)adenosine derivatives are described for treatment of ischaemic disease of the heart and brain.

The present invention relates to new adenosine analogues having potent binding in vitro to the adenosine A1 receptor, and at the same time showing selectivity for A 1 receptor binding in vitro over that to the A2 receptor subtype. In addition, many of the novel compounds contained in this invention have a relatively high lipophilicity, especially when compared to adenosine analogues and adenosine itself which are not substituted on the 6-amino group or the purine 2-position. This latter property may make these compounds suitable for passage across the blood brain barrier.

The possibility that some of the compounds may be substrates for nucleoside-specific active transport systems into the CNS across the blood barrier is, however, not excluded. These useful properties support the notion that some of the examples may have potential as candidate drugs for treatment of the CNS ailments mentioned within this invention in humans.

The compounds of the invention are purine derivatives of formula I, or a pharmaceutically acceptable salt thereof:

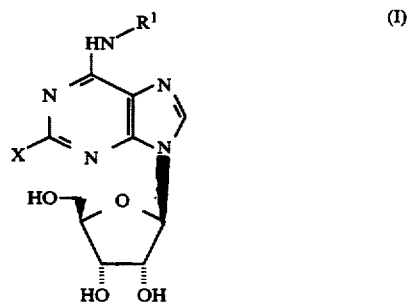

wherein
X represents hydrogen, halogen, amino, perhalomethyl, acetamido, cyano, $C_{1-6}$-alkyl, $C_{1-6}$-alkoxy, $C_{1-6}$-alkylthio or $C_{1-6}$-alkylamino;

$R^1$ is $-NR^2R^3$, $-YR^4$, wherein Y is oxygen or sulphur;

$R^2$ is $C_{1-6}$alkyl;

$R^3$ is phenyl or $C_{1-6}$-alkyl, which may be substituted with phenyl or phenoxy;

$R^4$ is naphthyl;

partly saturated naphthyl;

$C_{1-6}$-alkyl, which may be substituted with phenoxy or phenyl, which may be substituted with nitro, halogen or amino;

or $C_{3-8}$-cycloalkyl, which may be substituted with phenyl or phenoxy;

In certain examples, the group $R^1$ can contain one or more asymmetric carbon atoms in addition to those asymmetric centres already present in the molecule. In examples where this is the case, this invention includes all resulting diastereoisomers and mixtures thereof.

Various salts of compounds of formula (I) can be prepared which can be considered physiologically acceptable. These include addition salts derived from inorganic or organic acids, for example, acetates, fumarates, glutarates, glutaconates, lactates, maleates, methanesulphonates, phosphates, salicylates, succinates, sulphates, sulphamates, tartrates and paratoluenesulphonates. In some cases, solvates of either the free nucleosides or the acid addition salts can be isolated and these solvates may, for example, be hydrates or alcoholates.

Compounds of formula (I), which act as adenosine receptor agonists, are found to be useful in the treatment of central nervous system conditions such as anxiety, neuronal ischaemia/anoxia, convulsive disorders (epilepsy) and neurodegeneration (including Parkinson's disease).

Further, the compounds of formula (I) are found to be useful as analgesic agents, in lowering plasma free fatty acid (FFA) levels or as cardiovascular agents and also have application to myocardial ischaemia.

The invention also relates to methods of preparing the above mentioned compounds. These methods comprise:

Method A

A compound of formula (i) may be prepared by reacting a substance of formula (II), wherein L represents a leaving group such as a halogen atom (e.g. a chlorine or bromine atom) or a trimethylsilyloxy group, $P^1$, $P^2$ and $P^3$ are the same or different and represent hydrogen or a protecting group such as benzoyl-, p-toluoyl-, lower alkanoyl- (e.g. acetyl-), a substituted silyl group (e.g. a trimethylsilyl or t-butyldimethylsilyl group) or in the case of $P^3$, a triarylmethyl group, or in the case of $P^1$ and $P^2$, a 2',3'-O-(1-methyl)ethylidene derivative, with an O-alkylated hydroxylamine or a functionalised hydrazine derivative of general formula (III)

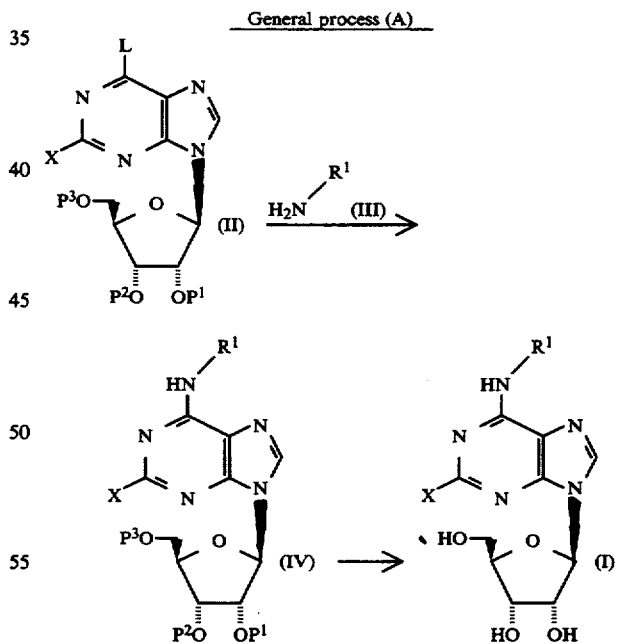

giving the compound of formula (IV) as the reaction product. In cases where $P^1$, $P^2$ and $P^3$ are not hydrogen an additional step will be required to remove protecting groups from (IV); in cases where the groups $P^1$, $P^2$ and $P^3$ are for example acetyl or benzoyl, suitable conditions for deprotection include methanolic ammonia, an alkali metal carbonate in methanol, an alkali metal alkoxide in the corresponding alcohol. Where the protecting groups are for example alkylsilicon or arylsilicon derivatives, suitable methods for deprotection include for example treatment with tetraalkylammonium fluorides or aqueous hydrolysis in the presence of acid or base. Where the $P^1$ and $P^2$ groups comprise a 2',3'-O-(1-methyl)ethylidene group, or $P^3$ comprises a triarylmethyl group, suitable conditions for deprotection include, for example, hydrolysis with aqueous mineral acid.

Method B

A compound of formula (I) (wherein X represents $-NH_2$, $-NH-C_{1-6}$-alkyl, or $-O-C_{1-6}$-alkyl, or $S-C_{1-6}$-alkyl) may be prepared by reacting a substance of general formula (V)

General process (B)

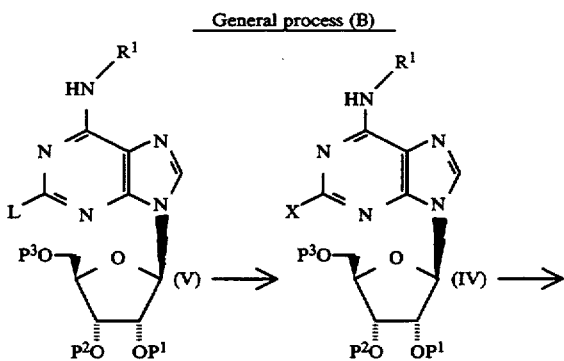

-continued
General process (B)

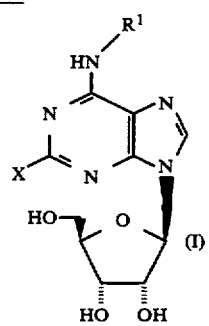

(where L is a leaving group as defined in method (A)) with a nucleophile, for example $C_{1-3}$-alkylamino (optionally in the presence of a suitable base) or with the anion ($C_{1-6}$-alkoxide or $C_{1-6}$-thioalkoxide) to afford the product (IV). In cases where $P^1$, $P^2$ and $P^3$ are hydrogen, compound (I) can be obtained directly. However, in cases where $P_2$ and $P_3$ are not hydrogen an additional step will be involved to remove protecting groups from (IV); examples of conditions for removal of protecting groups are given in process (A). In some reactions involving (V) with the anion $C_{1-6}$-alkoxide or $C_{1-6}$-thioalkoxide, where $P^1$, $P^2$ and $P^3$ are for example acetyl- or benzoyl-, partial or full deprotection may take place. In cases where only partial deprotection has taken place, deprotection can be completed under conditions described in method (A).

Method C

A compound of formula (I) may be prepared by reacting a substance of general formula (VI) (where B represents $-NH-R^1$ or L as defined previously) with a diazotising agent (such as, for example, 3-methylbutyl nitrite) to form an intermediate species which can be reacted further with a variety of substrates as exemplified below in order to introduce the group -X into the product (VII).

General process (C)

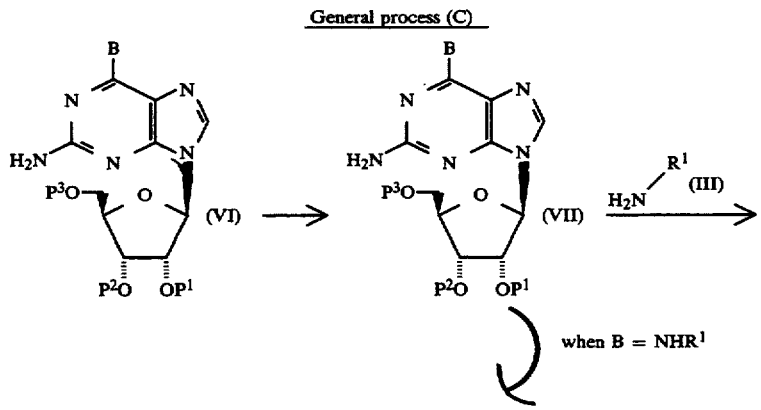

General process (C)

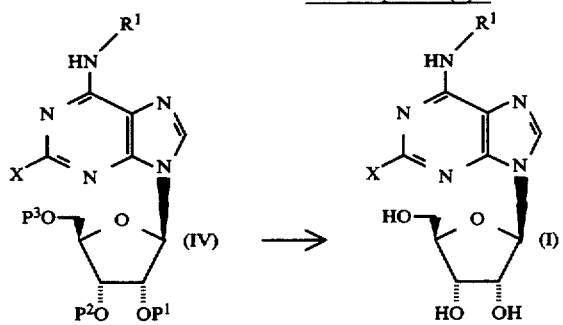

In the case where B represents a leaving group L, a further displacement reaction with for example (III) will be required in order to obtain the product (IV). In cases where the groups $P^1$, $P^2$ and $P^3$ are not hydrogen, or not all hydrogen, another step will be required to remove protecting groups from (IV); conditions for removing protecting groups are described in method A. Alternatively, where B represents HN—$R^1$, direct deprotection of intermediate (VII) can be carried out to provide (I).

Methods for assessing adenosine receptor binding in vitro have been reviewed [Adenosine Receptors, Cooper, D.M.F. and Londos, C., Eds., Alan R. Liss, Inc.: New York, 1988, 43–62].

Evaluation of these compounds in established animal models has indicated that the compounds according to the invention possess desirable central nervous system properties. For example, they act as anticonvulsant agents, are effective in animal models of pain, and show cerebroprotective effects in laboratory test animals subjected to simulated cerebral ischaemia. In addition, the compounds may have efficacy as neuroprotective agents in cases of cerebral oedema and traumatic head injury.

Evaluation of in vitro binding to adenosine A1 and A2 receptors

The affinity of the novel compounds described in this invention for the adenosine A1 receptor was determined essentially as described in the literature using [$^3$H]-R-PIA as a radioligand (Naunyn-Schmiedeberg's Archives of Pharmacology, 1980, 313, 179–187). Affinity for the A2 receptor was measured using the radioligand [$^3$H]-CGS 21680 (European Journal of Pharmacology, 1989, 168, 243–246), and the values for representative compounds is given in the table below.

Test results obtained by testing some compounds employed in the present invention are included in table I.

TABLE I

| Adenosine agonist tested | A1 receptor binding ($Ki_{50}$, nM) | A2 receptor binding ($Ki_{50}$, nM) | Ratio A2/A1 |
|---|---|---|---|
| Example 3 | 18 | 1659 | 92 |
| Example 7 | 6.7 | 2876 | 429 |
| Example 8 | 21 | 1154 | 55 |

The compounds of the invention, together with a conventional adjuvant, carrier or diluent, and if desired in the form of a pharmaceutically acceptable acid addition salt thereof, may be placed into the form of pharmaceutical compositions and unit dosages thereof, and in such form may be employed as solids, such as tablets of filled capsules, or liquids, such as solutions, suspensions, emulsions, elixirs, or capsules filled with the same, all for oral use, in the form of suppositories for rectal administration; or in the form of sterile injectable solutions for parenteral use (including subcutaneous administration and infusion). Such pharmaceutical compositions and unit dosage forms thereof may comprise conventional ingredients in conventional proportions, with or without additional active compounds or principles, and such unit dosage forms may contain any suitable effective amount of the adenosine receptor agonist commensurate with the intended daily dosage range to be employed. Tablets containing ten (10) milligrams of active ingredient or, more broadly, ten (10) to hundred (100) milligrams, per tablet, are accordingly suitable representative unit dosage forms.

The compounds of this invention can thus be used for the formulation of pharmaceutical preparation, e.g. for oral and parenteral administration to mammals including humans, in accordance with conventional methods of galenic pharmacy.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhyroxyethoxylated castor oil, gelatine, lactose amylose, magnesium stearate, talc, silicic acid, fatty acid monoglycerides and diglycerides, pentaerythritol fatty acid esters, hydroxymethylcellulose and polyvinylpyrrolidone.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compound dissolved in polyhydroxylated castor oil.

Ampoules are convenient unit dosage forms.

Tablets, dragees, or capsules having talc and/or carbohydrate carrier or binder or the like, the carrier preferably being lactose and/or corn starch and/or potato starch, are particularly suitable for oral application. A syrup, elixir or the like can be used in cases where a sweetened vehicle can be employed.

Generally, the compounds of this invention are dispensed in unit form comprising 0.05-100 mg in a pharmaceutically acceptable carrier per unit dosage.

The dosage of the compounds according to this invention is 0.1-300 mg/day, preferably 10-100 mg/day, when administered to patients, e.g. humans, as a drug.

A typical tablet which may be prepared by conventional tabletting techniques contains:

| | |
|---|---|
| Active compound | 5.0 mg |
| Lactosum | 67.0 mg Ph.Eur. |
| Avicel TM | 31.4 mg |
| Amberlite TM IRP 88 | 1.0 mg |
| Magnesii stearas | 0.25 mg Ph.Eur. |

Owing to activity against pain or convulsive disorders and prevention of neurodegeneration under conditions of anoxia/ischaemia the compounds of the invention are extremely useful in the treatment of related symptoms in mammals, when administered in an amount effective for agonist activity of compounds of the invention. The compounds of the invention may accordingly be administered to a subject, e.g., a living animal body, including a human, in need of adenosine receptor agonist, and if desired in the form of a pharmaceutically acceptable acid addition salt thereof (such as the hydrobromide, hydrochloride, or sulfate, in any event prepared in the usual or conventional manner, e.g., evaporation to dryness of the free base in solution together with the acid), ordinarily concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount of adenosine receptor agonist, and in any event an amount which is effective for the treatment of anoxia, traumatic injury, ischemia, migraine or other pain symptoms, epilepsy, or neurodegenerative diseases owing to their adenosine receptor agonist activity. Suitable dosage ranges are 1-200 milligrams daily, 10-100 milligrams daily, and especially 30-70 milligrams daily, depending as usual upon the exact mode of administration, form in which administered, the indication toward which the administration is directed, the subject involved and the body weight of the subject involved, and the preference and experience of the physician or veterinarian in charge.

The preparation of compounds of the invention is further illustrated in the following examples.

Hereinafter, TLC is thin layer chromatography, THF is tetrahydrofuran, TFA is trifluoracetic acid and mp is melting point. Where melting points are given, these are uncorrected. The structures of the compounds are confirmed by assignment of NMR spectra (from which representative peaks are quoted) and by microanalysis where appropriate. Compounds used as starting materials are either known compounds or compounds which can be prepared by methods known per se. Column chromatography was carried out on Merck silica gel 60 (Art 9385). HPLC was carried out on a Waters or Merck chromatograph with a multiwavelength detector and a reversed phase C18 column (250×4 mm, 5 μm, 100 Å; eluent flow rate 1 mL/min at 35° C). Retention times are given in minutes.

EXAMPLE 1 (Method A)

2-Chloro-N-(N-methyl-N-(2-phenylethyl)amino)adenosine.

N-Methyl-2-phenylethylamine hydrochloride.

Phenylacetaldehyde (24.0 g, 0.20 mol), a 33% solution of methylamine in ethanol (42.35 g, 0.41 mol) and methylamine hydrochloride (10.13 g, 14.8 mmol) were dissolved in methanol (200 ml). Sodium cyanoborohydride (3.77 g, 60 mmol) was introduced and the reaction mixture was stirred at room temperature for 18 h. The reaction mixture was evaporated in vacuo to ca. 50 ml, concentrated hydrochloric acid (40 ml) was added and once the exotherm had subsided the reaction mixture was stirred for 2 h. Water (200 ml) was introduced followed by potassium hydroxide (27 g, 0.48 mol) and the cooled solution was extracted with dichloromethane (7×100 ml). The combined dichloromethane extracts were extracted with 2N hydrochloric acid solution (200 ml) and 0.2N hydrochloric acid solution (200 ml). The combined acidic extracts were washed with dichloromethane (2×50 ml) and the aqueous phase was basified with 4N sodium hydroxide solution before being extracted with dichloromethane (2×100 ml). The combined extracts were dried (MgSO$_4$) and evaporated to a residue (9.2 g) which was dissolved in toluene (200 ml) with methanol (5 ml) present. Chlorotrimethylsilane (8.63 ml) dissolved in toluene (300 ml) was added and the hydrochloride salt of N-methyl-2-phenylethylamine precipitated. After cooling the suspension, the solid was collected by filtration and dried in vacuo; $^1$H NMR (DMSO-d$_6$)γ2.54 (3H, s, —CH$_3$), 2.92–3.07 (4H, m, —CH$_2$CH$_2$—), 7.20–7.40 (5H, m, Ar-H).

N-Methyl-N-nitroso-2-phenylethylamine

A sample of N-methyl-2-phenylethylamine hydrochloride (6.4 g, 37.3 mmol) was dissolved in water (18 ml), ethanol (11 ml) and 2N hydrochloric acid (4 ml) were introduced and the solution was heated to 70° C. A solution of sodium nitrite (2.6 g, 37.7 mmol) in water (11 ml) was added dropwise to the reaction mixture over 30 min. During the addition the reaction mixture was acidified with 2N hydrochloric acid (4 ml). Cooling was followed by extraction with n-heptane (4×100 ml); the combined extracts were dried (MgSO$_4$) and evaporated in vacuo to provide the N-methyl-N-nitroso-2-phenylethylamine as an oil (5.0 g, 81%) (a ca. 65:35 mixture of apparent geometric isomers), $^1$H NMR (DMSO-d$_6$) γ 2.98 (3H, s,—CH$_3$), 3.05 (2H, t, PhCH$_2$—), 4.37 (2H, t, —CH$_2$—N—), 7.13–7.36 (5H, m, Ar-H) (major isomer); 2.78 (2H, t, PhCH$_2$—), 2.98 (3H, s,—CH$_3$), 3.77 (2H, t,—CH$_2$—N—), 7.13–7.36 (5H, m, Ar-H) (minor isomer).

1-Methyl-1-(2-phenylethyl)hydrazine.

The above nitrosamine (5.0 g, 30.4 mmol) was dissolved in dry THF (100 ml) and a 1 M solution of lithium aluminium hydride in THF was added dropwise. On heating to 55° C. reaction commenced, the mixture was heated at reflux for 30 min. and cooled to room temperature. The reaction mixture was kept cool using a 23° C. water bath and water (50 ml) was carefully introduced dropwise with rapid stirring, followed by 1N sodium hydroxide solution (4 ml). The precipitate was removed by filtration and the flitrate was extacted with dichloromethane (3×50 ml). The combined extracts were dried (MgSO$_4$) and evaporated to a residue (4.08 g) which was dissolved in toluene (100 ml) with methanol (2 ml) present. Chlorotrimethylsilane (3.46 ml) dissolved in toluene (200 ml) was introduced and the hydrochloride salt of 1-methyl-1-(2-phenylethyl)hydrazine was separated as a gum, $^1$H NMR (CDCl$_3$)γ 2.44 (3H, s,—CH$_3$), 2.56 (2H, t,—CH$_2$), 2.76 (2H, t,—CH$_2$), 3.36 (2H, br s, —NH$_2$), 7.13-7.32 (5H, m, Ar-H).

9-(2,3,5-Tri-O-benzoyl-β-D-ribofuranosyl)-2,6-dichloro-9H-purine 2,6-dichloro-9(H)-purine (5.8 g, 30.7 mmol) and 1-O-acetyl-2,3,5-tri-O-benzoyl-D-ribofuranose (16.26 g, 32.2 mmol) were thoroughly mixed (as powdery solids) and fused together at 145°-150° C. under oil pump vacuum. The resultant oily mixture was stirred gently for 0.75 h (during which time the acetic acid by-product evaporated) and cooled to ca. 50° C. before being dissolved in dichloromethane (100 ml) with stirring. This solution was applied directly to a column of silica gel (6×22 cm) and eluted initially with cyclohexane/dichloromethane (1/1), then with dichloromethane and finally with cyclohexane/ethyl acetate (1/1) to provide 9-(2,3,5-tri-O-benzoyl-β-D-ribofuranosyl)-2,6-dichloro-9H-purine (16.6 g, 87%) as a colourless foam, TLC r$_f$ 0.50 [SiO$_2$, cyclohexane/ethyl acetate (1/1)]. $^1$H NMR (DMSO-d$_6$) γ 4.72 (1 H, dd, H-5'$_a$), 4.88 (1H, q, H-4'), 4.93 (1H, dd, H-5'$_b$), 6.15 (2H, m, H-2' & H-3'), 6.50 (1H, d, H-1'), 7.34-7.65 (9H, m, m- & p-ArH), 7.90-8.13 (6H, m, o-ArH), 8.28 (1H, s, H-8). (This method of preparation is a modification of that described by Imai, K-i. et al, Chemical and Pharmaceutical Bulletin, 1966, 14, 1377-1381, but without the use of a catalyst).

2',3',5'-Tri-O-benzoyl-2-chloro-N-(N-methyl-N-(2-phenylethyl) amino)adenosine

The above hydrochloride salt of 1-methyl-1-(2-phenylethyl)hydrazine (0.67 g, 1.05 mmol), 9-(2,3,5-tri-O-benzoyl-β-D-ribofuranosyl)-2,6-dichloro-9H-purine (1.90 g, 3 mmol) and triethylamine (1.24 ml, 9 mmol) were dissolved in 1,4 -dioxan (20 ml). The solution was stirred at ambient temperature for 20 h. The cooled reaction mixture was evaporated to a gum and purified by flash chromatography on silica gel. Bution with cyclohexane/ethyl acetate (4/1) initially and then with a 1/1 mixture of these solvents provided 2',3',5'-tri-O-benzoyl-2-chloro-N-(N-methyl-N-(2-phenylethyl-)amino)adenosine (1.28 g, 60%) as a foam, $^1$H NMR (DMSO-d$_6$)γ 2.63 (3H, s,—CH$_3$), 4.66 (1H, dd, H-5'$_a$), 4.77 (1H, dd, H-5'$_b$), 4.86 (1H, q, H-4'), 6.23 (1H, t, H-3'), 6.36 (1H, t, H-2'), 6.54 (1H, d, H-1'), 7.11-7.98 (20H, m, Ar-H), 8.44 (1H, s, H-8), 9.40 (1H, br s, N-H).

2',3', 5'-Tri-O-benzoyl-2-chloro-N-(N-methyl-N-(2-phenylethyl)amino)adenosine (1.24 g, 1.74 mmol) was dissolved in methanolic ammonia (50 ml) and allowed to stand at ambient temperature for 20 h. The reaction mixture was evaporated and the residue was purified by flash chromatography on silica gel. Elution with dichloromethane/methanol (19/1)initially, then increasing the polarity of the eluent to a 9/1 mixture of dichloromethane/methanol provided the title compound (0.57 g, 78%) as semi-solid foam, TLC rf 0.25 [SiO$_2$, dichloromethane/ethanol/25% aqueous ammonia solution (60/10/1)], $^1$H NMR (DMSO-d$_6$)γ 2.65 (3H, s,—CH$_3$), 3.53-3.60 (1H, m, H-5'$_a$), 3.63-3.70 (1H, m, H-5'$_a$), 4.05 (1H, q, H-4'), 4.15 (1H, q, H-3'), 4.55 (1H, q, H-2'), 5.08 (1H, t, 5'-OH), 5.22, 5.50 (2H, 2d, 2'- and 3'-OH), 5.56 (1H, d, H-1'), 7.11-7.28 (5H, m, Ar-H), 8.42 (1H, s, H-8), 9.33 (1H, br s, N-H).

C$_{19}$H$_{23}$ClN$_6$O$_4$.0.6 H$_2$O requires C, 51.2; H, 5.5; N, 18.9.

Found: C, 51.3; H 5.4; N 18.7%.

EXAMPLE 2

2-Chloro-N-[(N-methyl-N,phenyl)amino]adenosine

The title compound was prepared according to method A described in Example 1 by reacting 1-methylphenylhydrazine (1.29 g, 11 mmol) with 9-(2,3,5-tri-O-benzoyl-β-D-ribofuranosyl)-2,6-dichloro-9H-purine (1.58 g, 2.5 mmol) and debenzoylating the purified product using potassium carbonate in methanol to provide the title 2-chloro-N-[(N-methyl-N-phenyl-)amino]adenosine (0.70 g, 69%) (after column chromatography) as a colourless foam, TLC r$_f$ 0.50 [SiO$_2$, THF], $^1$H NMR (DMSO-d$_6$)γ 3.23 (3H, 2s, CH$_3$), 3.50-3.72 (2H, br,—CH$_2$—), 5.06 (1H, br, 5'-OH), 5.24, 5.52 (2H, 2d, 2'- and 3'-OH), 5.86 (1H, br, H-1'), 6.70-6.84 (3H, m, Ar-H), 7.15-7.24 (2H, t, Ar-H).

C$_{17}$H$_{19}$ClN$_6$O$_4$.0.66 H$_2$O requires C, 48.7; H, 4.9; N, 20.0. Found: C, 49.1; H 4.9; N 19.6%

EXAMPLE 3

2-Chloro-N-(N,N-dimethylamino)adenosine

The title compound was prepared according to method A described in Example 1 by reacting 1,1 -dimethylhydrazine (0.15 g, 2.52 mmol) with 9-(2,3,5-tri-O-benzoyl-β-D-ribofuranosyl)-2,6-dichloro-gH-purine (1.45 g, 2.29 mmol) and debenzoylating the purified product using methanolic ammonia to provide the title 2-chloro-N-(N,N-dimethylamino]adenosine (0.140 g, 29%) (after column chromatography) as a colourless foam, $^1$H NMR (DMSO-d$_6$)γ 2.58 (6H, s, 2 x —CH$_3$), 3.52-3.57 (1H, m, H-5'$_a$), 3.62-3.68 (1H, m, H-5'$_b$), 3.93 (1H, q, H-4'), 4.11 (1H, q, H-3'), 4.50 (1H, q, H-2'), 5.06 (1H, t, 5'-OH), 5.22, 5.48 (2H, 2d, 2'- and 3'-OH), 5.82 (1H, d, H-1'), 8.38 (1H, s, H-8), 9.34 (1H, br s, N-H).

C$_{12}$H$_{17}$ClN$_6$O$_4$.0.5 EtOH. 0.5 H$_2$O requires C, 41.5; H, 5.6; N, 22.3. Found: C, 41.5; H, 5.5; N, 22.1%.

EXAMPLE 4

2-Chloro-N-(phenylmethoxy)adenosine.

2',3',5'-Tri-O-benzoyl-2-chloro-N-(phenylmethoxy)adenosine (This example was also prepared by general method A). 9-(2,3,5-Tri-O-benzoyl-β-D-ribofuranosyl)-2,6-dichloro-9H-purine (2.0 g, 3.2 mmol), O-(phenylmethyl)hydroxylamine hydrochloride (0.77 g, 4.8 mmol) and diisopropylethylamine (1.03 g, 8.0 mmol) were dissolved in dioxan (50 ml). The reaction mixture was heated at reflux for 20 h, filtered and evaporated in vacuo. The crude product was coevaporated with dichloromethane and crystallised from a mixture of dichloromethane and methanol to provide the title compound (1.0 g, 43%), as white crystals, mp 115°-119° C., $^1$H NMR (CDCl$_3$)γ 3.52-3.70 (2H, m, H-5'$_a$ and H-5'$_b$) 3.95 (1H, d, H-4'), 4.15 (1H, dd, H-3'), 4.52 (1H, dd, H-2'), 5.00 (2H, s, CH2), 5.88 (1H, d, H-1'), 8.52 (1H, s, H-8).

C$_{38}$H$_{29}$ClN$_5$O$_8$ requires C, 63.4; H, 4.1; N, 9.7; Cl, 4.9. Found C, 63.5; H, 4.3; N, 9.5; Cl, 5.2%.

2',3',5'-Tri-O-benzoyl-2-chloro-N-(phenylmethoxy)adenosine (0.80 g, 1.1 mmol) was suspended in methanolic ammonia (50 ml). The reaction mixture was stirred at room temperature for 72 h. The solvent was evaporated in vacuo and the crude product was purified by flash chromatography (2×40 cm) eluting with dichloromethane/ethanol/aqueous ammonia solution (90/10/1) to give the title 2-chloro-N-(phenylmethoxy)adenosine as a foam (0.40 g, 89%), $^1$H NMR (DMSO-$d_6$)$\gamma$ 3.52–3.70 (2H, m, H-5′$_a$ and H-5′$_b$), 3.95 (1H, d, H-4′), 4.15 (1H, dd, H-3′), 4.52 (1H, dd, H-2′), 5.00 (2H, s, —CH$_2$—), 5.88 (1H, d, H-1′), 8.52 (1H, s, H-8). HPLC retention time 13.02 min (gradient elution over 30min; 20–80% acetonitrile/0.1% TFA in water; 99.6% purity/254 nm).

EXAMPLE 5

N-[(4-Nitrophenyl)methoxy]adenosine

The title compound was prepared according to Method A described above (R$^2$, R$^3$=H) by reacting O-[(4-nitrophenyl)methyl]hydroxylamine hydrochloride (1.43 g, 7 mmol) with 6-chloropurine riboside (i.e. 9-$\beta$-D-ribofuranosyl-6-chloro-9H-purine) (1.0 g, 3.5 mmol) in DMF (40 ml) at 110° C. for 2 h with diisopropylethylamine (1.80 g, 14 mmol) present. The reaction mixture was evaporated and to the resultant residue was added saturated sodium bicarbonate solution (20 ml) and water (20 ml). Methanol was gradually added until the residue dissolved, and the solid which gradually precipitated was removed by filtration. The flitrate was concentrated to a residue which was purified by flash chromatography on silica gel. Elution with ethyl acetate/ethanol (30/1) initially, followed by a (8/1) mixture of these solvents provided a solid which was recrystallized from ethanol. The first crop of material was discarded, but the second crop was confirmed as the title compound (70 mg, 7%) mp 115°–117° C. TLC r$_f$0.20 [SiO$_2$, ethyl acetate/methanol (9/1)]; $^1$H NMR (DMSO-$d_6$)$\gamma$ 3.46–3.57 (2H, m, H-5′$_a$ and H-5′$_b$), 3.90 (1H, q, H-4′), 4.08 (1H, q, H-3′), 4.43 (1H, q, H-2′), 5.07 (1H, t, 5′-OH), 5.44, 5.74 (2H, 2d, 2′and 3′-OH), 5.82 (1H, d, H-1′), 7.67 (2H, d, Ar-H), 8.08 (1h, s, H-8), 8.22 (2H, d, Ar-H), 9.34 (1H, br s, N-H).

$C_{17}H_{18}N_6O_7.0.75$ H$_2$O requires C, 47.3; H, 4.6; N, 19.45. Found: C, 48.8; H, 4.55; N, 19.45%.

EXAMPLE 6 (Method A)

2-Chloro-N-(2-phenylethoxy) adenosine.

N-(2-Phenylethoxy)phthalimide

N-Hydroxyphthalimide (15.0 g, 92 mmol) and sodium acetate (7.5 g, 92 mmol) were stirred in dimethylsulfoxide (70 ml) at ambient temperature for 3 h. 2-Chloroethylbenzene (12.5 g, 89 mmol) was added and the reaction mixture was heated at reflux for 2 h. After cooling and standing overnight the reaction mixture was filtered and the flitrate was poured onto ice/water (300 ml). The mixture was extracted with dichloromethane (4×100 ml), the combined extracts were dried (MgSO$_4$) and evaporated in vacuo to a residue. Purification by flash chromatography on a silica gel column eluting with heptane/ethyl acetate (1/1) afforded the title compound as a colourless foam (15.7 g, 33%); $^1$H NMR (DMSO-$d_6$)$\gamma$ 3.05 (2H, t, —OCH$_2$—), 4.39 (2H, t, —CH$_2$Ph), 7.20–7.35 (5H, m, Ar-H), 7.85 (4H, s, Ar-H).

O-(2-Phenylethyl)hydroxylamine hydrochloride.

N-(2-Phenyloxy)phthalimide (11.3 g, 42 mmol) was dissolved in hot 96% ethanol (100 ml). Hydrazine hydrate (2.5 g, 50 mmol) was introduced and the reaction mixture was heated at reflux with mechanical stirring for 1.5 h. The reaction mixture was stored at 4° C. for 72 h, filtered and the flitrate was evaporated in vacuo. The crude white residue was suspended in toluene and stored at 4° C. for 16 h and filtered. The flitrate was treated with a solution of chlorotrimethylsilane (4.34 g) in toluene (200 ml) with methanol (1.05 g) present and the title compound precipitated. The suspension was allowed to cool and the product was collected and dried in vacuo, giving a white hygroscopic solid product (5.84 g, 84%). $^1$H NMR (DMSO-$d_6$)$\gamma$ 2.95 (2H, t, —OCH$_2$—), 4.25 (2H, t, —CH$_2$Ph), 7.20–7.35 (5H, m, Ar-H).

2′, 3′, 5′-Tri-O-benzoyl-2-chloro-N-(2-phenylethoxy)adenosine.

9-(2,3,5-Tri-O-benzoyl-$\beta$-D-ribofuranosyl)-2,6-dichloro-9H-purine (2.0 g, 3.2 mmol), O-(2-phenylethyl)hydroxylamine hydrochloride (0.70 g, 4.0 mmol) and diisopropylethylamine (0.95 g, 7.4 mmol) were dissolved in 1,4-dioxan (40 ml) and heated at reflux for 3 days. After cooling the reaction mixture was diluted with dichloromethane (50 ml) and washed with water (2×30 ml). The organic phase was dried (MgSO$_4$). Flash chromatography on a silica gel column, eluting with heptane/ethyl acetate (1/1) gave the desired product as a foam (1.54 g, 66%), $^1$H NMR (DMSO-$d_6$)$\gamma$ 3.05 (2H, t, —OCH$_2$—), 4.19 (2H, t,—CH$_2$Ph), 4.70 (1H, dd, H-5′$_a$), 4.80 (1H, dd, H-5′$_b$), 4.90 (1H, dd, H-4′), 5.22 (1H, t, H-3′), 6.39 (1H, t, H-2′), 6.59 (1H, d, H-1′), 8.51 (1H, s H-8).

$C_{38}H_{23}ClN_5O_8$ requires C, 63.8; H, 4.4; N, 9.5. Found C, 63.7; H, 4.5; N, 9.4%.

2′,3′,5′,-Tri-O-benzoyl-2-chloro-N-(2-phenylethoxy)adenosine ( 1.54 g, 2.0 mmol) was suspended in a solution of methanolic ammonia and stirred at room temperature for 2 days. The reaction mixture was concentrated in vacuo and the crude product was purified by flash chromatography eluting with dichloromethane/ethanol/aqueous ammonia solution (90/10/1), providing the product as a foam (0.48 g, 57%), $^1$H NMR (DMSO-$d_6$)$\gamma$ 3.00 (2H, t,—CH$_2$O—), 3.55–3.70 (2H, m, H-5′$_a$ and H-5′$_b$), 3.99 (1H, d, H-4′), 4.15–4.20 (3H, m,—CH$_2$Ph and H-3′), 4.52 (1H, dd, H-2′), 5.88 (1H, d, H-1′), 8.51 (1H, s, H-8). HPLC retention time 13.64 min (gradient elution over 30 min; 20–80% acetonitrile/0.1% trifluoroacetic acid in water; 99.0% purity/254 nm).

$C_{18}H_{20}ClN_5O_5.0.75$ H$_2$O requires C, 49.7; H, 5.0; N, 16.1. Found C, 49.9; H, 4.9; N, 15.8%.

EXAMPLE 7 (Method A)

2-Chloro-N-cyclopentyloxyadenosine

The title compound was prepared according to method A as described in example 6 by reacting O-cyclopentylhydroxylamine (prepared by the overall procedure described in example 5) (0.78 g, 5.67 mmol) with 9-(2,3,5-tri-O-benzoyl-$\beta$-D-ribofuranosyl)-2,6-dichloro-9H-purine (3.0 g, 4.74 mmol), followed by debenzoylation of the purified product using methanolic ammonia to provide the title 2-chloro-N-cyclopentyloxyadenosine (0.11 g) (after column chromatography) as a solid, mp 116°–119° C., $^1$H NMR (DMSO-$d_6$)$\gamma$ 1.50–1.80 (8H, m, —CH$_2$CH$_2$CH$_2$CH$_2$—), 3.52–3.58 (1H, m, H-5′$_a$), 3.63–3.70 (1H, m, H-5′$_b$), 3.94 (1H, q, H-4′), 4.13 (1H, q, H-3′), 4.51 (1H, q, H-2′), 4.57 (1H, br m,—OCH—), 5.06 (1H, t, 5′—OH), 5.22, 5.50 (2H, 2d, 2′-and 3′—OH), 5.86 (1H, d, H-1′), 8.46 (1H, s, H-8), 11.40 (1H, s, N-H).

EXAMPLE 8 (Method A)

2-Chloro-N-methoxyadenosine.

The title compound was prepared according to method A as described in example 4 by reacting O-methylhydroxylamine (0.20 g, 2.0 mmol) with 9-(2,3,5- tri-O-benzoyl-β-D-ribofuranosyl)-2,6-dichloro-9H-purine (1.27 g, 2.0 mmol) and debenzoylating the purified product using methanolic ammonia to provide the title 2-chloro-N-methoxyadenosine (0.40 g, 45%) (after column chromatography) as a colourless foam which became crystalline on trituration with dichloromethane, providing 0.20 g of a white solid, mp 123°-125° C. $^1$H NMR (DMSO-d$_6$)γ 3.52-3.59 (1H, m, H-5'$_a$), 3.63-3.70 (1H, m, H-5'$_b$), 3.78 (3H, s, —OCH$_3$), 3.96 (1H, q, H-4'), 4.14 (1H, q, H-3'), 4.52 (1H, q, H-2'), 5.06 (1H, t, 5'-OH), 5.22, 5.51 (2H, 2d, 2'- and 3'-OH), 5.87 (1H, d, H-1'), 8.50 (1H, s, H-8), 11.60 (1H, s, N-H).

C$_{11}$H$_{14}$ClN$_5$O$_5$.1.33 H$_2$O requires C, 37.1; H, 4.7; N, 19.7. Found: C, 37.4; H, 4.4; N, 19.3%.

EXAMPLE 9 (Method A)

2-Chloro-N-[2-(phenoxy)ethoxy]adenosine.

The title compound was prepared according to method A as described in examples 4 and 5 by reacting O-[2-(phenoxy)ethyl]hydroxylamine (prepared by the procedure described in example 6) (0.94 g, 5.0 mmol) with 9-(2,3,5-tri-O-benzoyl-β-D-ribofuranosyl)-2,6-dichloro-9H-purine (2.0 g, 3.16 mmol), followed by debenzoylation of the purified product using methanolic ammonia to provide the title 2-chloro-N-[2-(phenoxy)ethoxy]adenosine (0.44 g, 32%) (after column chromatography) as a colourless foam, $^1$H NMR (DMSO-d$_6$)γ 3.52-3.59 (1H, m, H-5'$_a$), 3.63-3.70 (1H, m, H-5'$_b$), 3.94 (1H, q, H-4'), 4.11 (1H, q, H-3'), 4.32 (4H, dt,-OCH$_2$CH$_2$O—), 4.50 (1H, q, H-2'), 5.06 (1H, t, 5'-OH), 5.22, 5.50 (2H, 2d, 2'- and 3'-OH), 5.86 (1H, d, H-1'), 6.92-6.97 (3H, m, Ar-H), 7.26-7.33 (2H, dd, Ar-H), 8.51 (1H, s, H-8), 11.64 (1H, br, N-H).

C$_{18}$H$_{20}$ClN$_5$O$_4$.0.66 H$_2$O requires C, 48.1; H, 4.8; N, 15.6. Found: C, 48.1; H, 4.7; N, 15.4%.

EXAMPLE 10 (Method A)

2-Chloro-N-(1,2,3,4-tetrahydronaphth-1-yloxy)adenosine.

The title compound was prepared according to method B as described in examples 4 and 5 by reacting O-[1,2,3,4-tetrahydronaphth-1-yl)hydroxylamine (prepared by the procedure described in example 6) (0.35 g, 2.0 mmol) with 9-(2,3,5-tri-O-benzoyl-β-D-ribofuranosyl)-2,6-dichloro-9H-purine (1.0 g, 1.58 mmol) and debenzoylating the purified product using methanolic ammonia to provide the title 2-chloro-N-(1,2,3,4-tetrahydronaphth-1-yloxy)adenosine (0.10 g, 15%) (after column chromatography) as a colourless foam (a mixture of diastereoisomers), $^1$H NMR (DMSO-d$_6$)γ 1.65 - 2.85 (6H, m,—CH$_2$CH$_2$CH$_2$—), 3.53-3.61 (1H, m, H-5'$_a$), 3.64-3.70 (1H, m, H-5'$_b$), 3.94 (1H, br d, H-4'), 4.16 (1H, br d, H-3'), 4.53 (1H, q, H-2'), 5.07 (2H, m, 5'-OH and OCH—), 5.26, 5.53 (2H, 2d, 2'- and 3'-OH), 5.88 (1H, d, H-1'), 7.13-7.30 (3H, m, Ar-H), 7.88-7.96 (1H, m, Ar-H), 8.52 (1H, s, H-8), 11.60 (1H, br s, N-H). HPLC retention time 20.71 and 20.95 min (gradient elution over 25 min.; 25-45% acetonitrile/0.1M.

EXAMPLE 11 (Method B)

2,N-Dimethoxyadenosine.

2-Chloro-N-methoxyadenosine (Example 8) (0.20 g, 0.60 mmol) was added to a mixture of sodium hydride (40 % oil dispersion) (0.12 g, 3.0 mmol) methanol (0.24 ml) amd DMF (5 ml) which had been stirred under nitrogen at room temperature for 1 h. The reaction mixture was heated at 80° C. for 16 h, cooled and evaporated. Flash chromatography provided the title 2,N-dimethoxyadenosine, still however containing some starting 2-chloro-N-methoxyadenosine. $^1$H NMR (DMSO-d$_6$)γ 3.52-3.59 (1H, m, H-5'$_a$), 3.63-3.70 (1H, m, H-5'$_b$), 3.77 (3H, s, —OCH$_3$), 3.97 (1H, q, H-4'), 4.14 (1H, q, H-3'), 4.60 (1H, q, H-2'), 5.09 (1H, t, 5'-OH), 5.18, 5.44 (2H, 2d, 2'- and 3'-OH), 5.83 (1H, d, H-1'), 8.24 (1H, s, H-8), 11.04 (1H, s, N-H) (desired product only quoted).

EXAMPLE 12 (Method C)

2-Methylthio-N-[2-(phenoxy)ethoxy]adenosine.

9-(2,3,5-Tri-O-acetyl-β-D-ribofuranosyl)-6-chloro-2-methylthio-9H-purine (0.50 g, 1.1 mmol) (prepared by Method C, using the procedure described in PCT Publication No. WO 93/08206, O-[2-(phenoxy)ethoxy]hydroxylamine hydrochloride (0.41 g, 2.16 mmol) (see Example 9) and triethylamine (0.45 g, 4.4 mmol) were stirred at 100° C. in dioxan (20 ml) for 6 h, and at ca. 95° C. for 65 h. The product, after column chromatography, was deprotected using methanolic ammonia, to provide the title 2-methylthio-N-[2-(phenoxyethoxy]adenosine (0.09 g, 18%), (after column chromatography) as a colourless foam, tlc R$_f$ 0.26 [(SiO$_2$, dichloromethane/methanol (9/1)], $^1$H NMR (DMSO-d$_6$)γ 2.51 (3H, s,—SCH$_3$), 3.52-3.60 (1H, m, H-5'$_a$), 3.62-3.69 (1H, m, H-5'$_b$), 3.94 (1H, q, H-4'), 4.16 (1H, q, H-3'), 4.30 (4H, br d,—OCH$_2$CH$_2$O—), 4.61 (1H, q, H-2'), 5.04 (1H, t, 5'-OH), 5.23, 5.50 (2H, 9d, 9'- and 3'-OH), 5.90 (1H, d, H-1'), 6.92-7.01 (3H, m, Ar-H), 7.32 (2H, dd, Ar-H), 8.36 (1H, s, H-8), 11.20 (1H, s, N-H).

EXAMPLE 13 (Method A)

2-Amino-N-(N,N-dimethylamino)adenosine.

The title compound was prepared according to method A as described in example 4 by reacting 1,1-dimethylhydrazine (0.79 g, 13.1 mmol) with 9-(2,3,5-tri-O-acetyl-β-D-ribofuranosyl)-2-amino-6-chloro-9H-purine (4.0 g, 9.35 mmol) and debenzoylating the purified product using methanolic ammonia to provide the title 2-amino-N-(dimethylamino)adenosine (after column chromatography) as an amorphous foam (0.56 g, 45%), $^1$H NMR (DMSO-d$_6$)γ 2.54 (6H, s, 2×—CH$_3$), 3.50-3.57 (1H, m, H-5'$_b$), 3.61-3.68 (1H, m, H-5'$_b$), 3.93 (1H, q, H-4'), 4.12 (1H, q, H-3'), 4.51 (1H, q, H-2'), 5.12, 5.38 (2H, 2d, 2'- and 3'-OH), 5.42 (1H, t, 5'-OH), 5.76 (1H, d, H-1'), 5.95 (2H, s, —NH$_2$), 7.93 (1H, s, H-8), 8.20 (1H, s, N-H).

EXAMPLE 14 (Method A)

2-Chloro-N-(N-methyl-N-(2-phenoxyethyl-)amino)adenosine

The title compound was prepared according to method A by reacting 1-methyl-1-(2-phenoxyethyl)hydrazine (prepared by the general method described in example 1) (0.80 g, 4 mmol) and 9-(2,3,5-tri-O-benzoyl-β-D-ribofuranosyl)-2,6-dichloro-9H-purine (2.53 g, 4 mmol) and triethylamine (1.11 ml, 8 mmol) in dioxan (25 ml), followed by debenzoylation of the purified product using methanolic ammonia to provide the title 2-chloro-N-(N-methyl-N-(2-phenoxyethyl)amino)adenosine (0.84 g, 47%) (after column chromatography) obtained as a solid, mp 166°-8° C., $^1$H NMR (DMSO-d$_6$)γ 2.70 (3H, s, —CH$_3$), 3.22 (2H, br t, —CH$_2$—), 3.51-3.58 (1H, m, H-5'$_a$), 3.62-3.69 (1H, m, H-5'$_a$), 3.95 (1H, q, H-4'), 4.05-4.15 (3H, m, —CH$_2$— and H-3'), 4.50 (1H, q, H-2'), 5.06 (1H, t, 5'-OH), 5.21, 5.49 (2H, 2d, 2'- and 3—OH), 5.81 (1H, H-1'), 6.79-7.25 (5H, m, Ar-H), 8.41 (1H, s, H-8), 9.41 (1H, br s, N-H).

EXAMPLE 15 (Method A)

N-Cyclopegtoxy-2-methyladenosine

O-Cyclopentylhydroxylamine hydrochloride (0.52 g, 3.75 mmol) was reacted with 9-(2,3,5-triO-acetyl-β-D-ribofuranosyl)-6-chloro-2-methyl-9H-purine (1.07 g, 2.5 mmol) [prepared from 2-methylinosine (Journal of Organic Chemistry, 1967, 32, 3258-3260) by standard acylation and chlorination steps] in dioxan (40 ml) in the presence of triethylamine (0.63 g, 6.25 mmol). The reaction mixture was heated at 100° C. for 70 h, before being filtered and evaporated. The product (after purification by chromatography), followed by debenzoylation using methanolic ammonia to provide the title N-cyclopentoxy-2-methyladenosine (after column chromatography) as a foam $^1$H NMR (DMSO-d$_6$)γ 1.47-1.93 (8H, m,—CH$_2$CH$_2$CH$_2$CH$_2$—), 2.32 (3H, s,—CH$_3$), 4.59 (1H, br m,—O—CH—), 5.88 (1H, d, H-1').

We claim:

1. A compound of formula I:

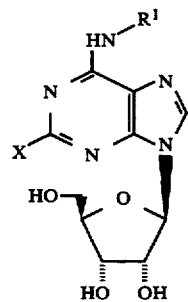

(I)

wherein

X is halogen, perhalomethyl, acetamido, cyano, C$_{1-6}$-alkoxy, C$_{1-6}$-alkylthio or C$_{1-6}$-alkylamino; and R$^1$ is —NR$^2$R$^3$ or —YR$^4$, wherein Y is oxygen or sulphur; R$^2$ is C$_{1-6}$-alkyl; R$^3$ is phenyl, C$_{1-6}$-alkyl, or C$_{1-6}$-alkyl which is substituted with phenyl or phenoxy; and R$^4$ is naphthyl; partly saturated naphthyl; C$_{1-6}$-alkyl which may be substituted with a phenoxy or phenyl group, wherein the phenoxy or phenyl group may be substituted with nitro, halogen or amino; or C$_{3-8}$-cycloalkyl which may be substituted with phenyl or phenoxy; or a pharmaceutically acceptable salt thereof.

2. A compound according to claim 1, wherein R$^1$ is —NR$^2$R$^3$ or —YR$^4$, wherein Y is oxygen; R$^2$ is C$_{1-6}$-alkyl; R$^3$ is phenyl, C$_{1-6}$-alkyl, or C$_{1-6}$-alkyl which is substituted with phenyl or phenoxy; and R$^4$ is naphthyl; partly saturated naphthyl; C$_{1-6}$-alkyl which may be substituted with a phenoxy or phenyl group, wherein the phenoxy or phenyl group may be substituted with nitro, halogen or amino; or C$_{3-8}$- cycloalkyl which may be substituted with phenyl or phenoxy.

3. A compound according to claim 1, wherein R$^1$ is —NR$^2$R$^3$, wherein R$^2$ is C$_{1-6}$-alkyl and R$^3$ is phenyl, C$_{1-6}$-aLkyl, or C$_{1-6}$-alkyl which is substituted with phenyl or phenoxy.

4. A compound according to claim 1, wherein R$^1$ is —YR$^4$, wherein Y is oxygen or sulphur and R$^4$ is naphthyl; partly saturated naphthyl; C$_{1-6}$-alkyl which may be substituted with a phenoxy or phenyl group, wherein the phenoxy or phenyl group may be substituted with nitro, halogen or amino; or C$_{3-8}$-cycloalkyl which may be substituted with phenyl or phenoxy.

5. A compound according to claim 1, wherein X is C$_{1-6}$-alkoxy.

6. A compound according to claim 1, wherein X is halogen.

7. A compound according to claim 1, wherein X is chlorine.

8. A compound according to claim 3, wherein R$^1$ is —NR$^2$R$^3$ wherein R$^2$ is methyl and R$^3$ is phenyl, C$_{1-6}$-alkyl, or C$_{1-6}$-alkyl which is substituted with phenyl or phenoxy.

9. A compound according to claim 4, wherein R$^1$ is —OR$^4$ wherein R$^4$ is C$_{1-6}$-alkyl which may be substituted with a phenoxy or phenyl group, wherein the phenoxy or phenyl group may be substituted with nitro, halogen or amino.

10. A compound according to claim 1 which is selected from the group consisting of
2-chloro-N-(N-methyl-N-(2-phenylethyl)amino)adenosine,
2-chloro-N-[(N-methyl-N-phenyl)amino]ladenosine,
2-chloro-N-(N,N-dimethylamino)adenosine,
2-chloro-N-(N-methyl-N-(2-phenoxyethyl)amino)adenosine, and
pharmaceutically acceptable salts thereof.

11. A compound according to claim 1 which is selected from the group consisting of
2-chloro-N-(phenylmethoxy)adenosine,
2-chloro-N-(2-phenylethoxy)adenosine,
2-chloro-N-cyclopentyloxyadenosine,
2-chloro-N-methoxyadenosine,
2-chloro-N-[2-(phenoxy)ethoxy]adenosine,
2-chloro-N-(1,2,3,4-tetrahydronaphth-1-yloxy)adenosine, and
pharmaceutically acceptable salts thereof.

12. A compound according to claim 1 which is selected from the group consisting of
2,N-dimethoxyadenosine,
2-methylthio-N-[2-(phenoxy)ethoxy]adenosine, and
pharmaceutically acceptable salts thereof.

13. N-cyclopentoxy-2-methyladenosine or a pharmaceutically acceptable salt thereof.

14. A pharmaceutical composition comprising a compound according to claim 1 and a pharmaceutically acceptable carrier.

15. A pharmaceutical composition according to claim 14 in the form of an oral dosage unit containing about 1-200 mg of the active compound.

16. A method of treating myocardial ischemia in a person in need thereof, comprising administering an effective amount of a compound according to claim 1.

17. A method of treating myocardial ischemia in a subject in, need thereof, comprising administering a pharmaceutical composition according to claim 1.

18. A method of treating cerebral ischemia in a person in need thereof, comprising administering an effective amount of a compound according to claim 1.

19. A method of treating cerebral ischemia in a subject in need thereof, comprising administering a pharmaceutical composition according to claim 14.

* * * * *